United States Patent [19]

Morgan et al.

[11] Patent Number: 5,690,939
[45] Date of Patent: Nov. 25, 1997

[54] RECOMBINANT VACCINE AGAINST MAREK'S DISEASE

[75] Inventors: Robin Wilson Morgan, Landenberg, Pa.; Johannes Antonius Joseph Claessens; Paulus Jacobus Antonius Sondermeijer, both of Boxmeer, Netherlands

[73] Assignee: Akzo Nobel N.V., Arnhem, Netherlands

[21] Appl. No.: 440,846

[22] Filed: May 15, 1995

Related U.S. Application Data

[62] Division of Ser. No. 67,416, May 24, 1993, which is a continuation of Ser. No. 917,721, Jul. 20, 1992, abandoned, which is a continuation of Ser. No. 699,467, May 14, 1991, abandoned.

[51] Int. Cl.$^6$ ....................... A61K 39/255; C07K 14/055
[52] U.S. Cl. ......................... 424/229.1; 530/350
[58] Field of Search ................... 530/350, 344; 424/204.1, 229.1; 514/2

[56] References Cited

U.S. PATENT DOCUMENTS 5,283,191 2/1994 Morgan et al. ............. 435/252.3

FOREIGN PATENT DOCUMENTS 0893024851 9/1989 European Pat. Off. .
WO 8901040 2/1989 WIPO .

OTHER PUBLICATIONS

T. Igarashi et al., "Restriction Enzyme Map of Herpesvirus of Turkey DNA and its Collinear Relationship with Marek's Disease Virus DNA," *Virology*, vol. 157 pp. 351-358, 1987, USA.

K. Fukuchi et al., "Structure of Marek's Disease Virus DNA: Detailed Restriction Enzyme Map," *Journal of Virology*, vol. 51, pp. 102-109, 1984, USA.

N. Yanagida et al., "Recombinant Fowlpox Viruses Expressing the Glycoprotein B Homolog and the pp38 Gene of Marek's Disease Virus," *Journal of Virology*, 66:3:1402-1408, Mar. 1992.

X. Chen et al., "Identification of a Unique Marek's Disease Virus Gene Which Encodes a 38kD Phosphoprotein and is Expressed in both Lytcally Infected Cells and Latently Infected Lymphoblastoid Tumor Cells," *Journal of Virology*, 66:1:85-94, Jan. 1992.

Z. Cui et al., "Marek's Disease Virus Gene Clones Encoding Virus-Specific Phosphorylated Polypeptides and Serological Characterization of Fusion Proteins,"*Virus Genes*, 3:4:309-322, 1990, The Netherlands.

Z. Cui et al., "Structural Analysis and Transcriptional Mapping of the Marek's Disease Virus Gene Encoding pp38, an Antigen Associated with Transformed Cells" *Journal of Virology*, 65:12:6509-6515, Dec. 1991, USA.

I. Sithole et al., "Synthesis and Processing of the Marek's Disease Herpes-virus B Antigen Glycoprotein Complex," *Journal of Virology*, 62:11:4270-4279 Nov. 1988.

*Primary Examiner*—David Guzo
*Attorney, Agent, or Firm*—Gregory R. Muir; William M. Blackstone

[57] ABSTRACT

The invention is related to a nucleic acid sequence encoding a MD06 Marek's Disease Virus protein. Such a protein can be used for the immunization of poultry against MDV infection or disease. The nucleic acid sequence encoding the MD06 MDV protein can be applied for the preparation of the protein by means of genetic engineering techniques or can be applied for the preparation of vector vaccines.

6 Claims, 5 Drawing Sheets

RECOMBINANT VACCINE AGAINST MAREK'S DISEASE

This is a division of U.S. Ser. No. 08/067,416, filed May 24, 1993, which is a file wrapper continuation of U.S. Ser. No. 07/917,721, filed Jul. 20, 1992, now abandonded, which is a file wrapper continuation of U.S. Ser. No. 07/699,467, filed May 14, 1991, now abandoned.

The present invention is concerned with a nucleic acid sequence encoding a Marek's Disease virus polypeptide, a recombinant nucleic acid molecule comprising such a nucleic acid sequence, a vector virus comprising said nucleic acid sequence, a host cell transformed with such a nucleic acid sequence, a Marek's Disease virus polypeptide and antibodies reactive with the polypeptide, as well as a vaccine against Marek's Disease.

Marek's Disease (MD) is a malignant, lymphoproliferative disorder of domestic fowl caused by a herpesvirus: Marek's Disease Virus (MDV). MD is ubiquitous, occurring in poultry-producing countries throughout the world. Chickens raised under intensive production systems will inevitably suffer losses from MD. MD affects chickens from about 6 weeks of age, occurring most frequently between ages of 12 and 24 weeks.

Three forms of MD are recognized clinically, classical MD, acute MD and transient paralysis.

Classical MD is characterized by peripheral nerve enlargement caused by lymphoid infiltration and demyelination, and paralysis is the dominant clinical sign. Mortality is variable but normally under 10–15 per cent.

In the acute form there are multiple and diffuse lymphomatous tumours in the visceral organs. Mortality from this form of MD is usually higher than from the classical form. An incidence of 10–30 per cent is common in unvaccinated flocks and outbreaks involving up to 70% of the flock may be encountered. The pathological lesions in both classical and acute MD are essentially similar, involving the proliferation and infiltration of malignantly transformed T-lymphoblasts into normal tissues, peripheral nerves in the case of the classical form and visceral organs in the case of the acute form.

Furthermore, the MDV has been shown to be responsible for encephalitis of young chickens characterized by sudden paralysis.

Serological classification of MD related viruses yielded three serotypes:

Type I : naturally occurring virulent strains of Marek's disease virus which are pathogenic and tumorigenic to chickens, and attenuated nonpathogenic strains derived thereof Type II : naturally occurring nonpathogenic strains of Marek's disease virus; and Type III: herpesvirus of turkeys ("HVT"), which is non-pathogenic to chickens.

Serial passage of pathogenic strains of MDV serotype I was found to result in loss of pathogenicity and oncogenicity, but not of immunogenicity. Attenuated strains derived from HPRS-16 and CVI-988 strains have been applied as vaccines. SB-I and HN-I MDV strains (serotype 2) have also been shown to be useful in vaccination. HVT, first isolated from turkeys, is apathogenic in turkeys and domestic fowls, antigenically related to serotype 1 and 2 MD viruses and extensively used as a vaccine against MD.

There are no methods of treatment of MD and control is based on management methods which isolate growing chickens from sources of infection or disease, the use of genetically resistant stock, and vaccination. However, management procedures are normally not cost-effective and the progress has been disappointing with respect to the selection of poultry stock with increased genetically controlled resistance. Nowadays, control of MD is almost entirely based on vaccination.

Current vaccines comprise chemically inactivated virus vaccines or modified live-virus vaccines. However, inactivated vaccines require additional immunizations, disadvantageously contain adjuvants, are expensive to produce and are laborious to administer. Further, some infectious virus particles may survive the inactivation process and may cause disease after administration to the animal.

In general, attenuated live virus vaccines are preferred because they evoke an immune response often based on both humoral and cellular reactions. Up to now, such vaccines based on MDV serotype I strains could only be prepared by serial passage of virulent strains in tissue culture. However, because of this treatment uncontrolled mutations are introduced into the viral genome, resulting in a population of virus particles heterogeneous with regard to virulence and immunizing properties. Over attenuation during passage in cell culture can also be a problem with these vaccines. One must achieve a delicate balance between ensuring that the vaccine is not virulent while making certain that it is still protective. In addition it is well known that such traditional attenuated live virus vaccines can revert to virulence resulting in disease outbreaks in inoculated animals and the possible spread of the pathogen to other animals. The occurrence of very virulent field strains of MD virus, against which live HVT vaccines provided poor protection, have now been reported and are responsible for excessive losses in various parts of the world. Bivalent vaccines consisting of serotype 2 and serotype 3 strains are reasonably effective against very virulent field isolates in some cases. Multivalent vaccines containing serotype 1 antigens should be even more effective at eliciting immunity against these very virulent strains.

Improved vaccines might be constructed based on recombinant DNA technology. These vaccines would only contain the necessary and relevant MDV immunogenic material which is capable of eliciting a protective immune response against the MDV pathogens, or the genetic information encoding said material, and would not display above-mentioned disadvantages of the live or inactivated vaccines.

According to the present invention an isolated and purified nucleic acid sequence encoding a polypeptide having one or more immunogenic determinants of a MDV protein MD06 and having an amino sequence as shown in SEQ ID NO:2 or a functional variant thereof is provided which can be applied for the preparation of a vaccine for the immunization of poultry against MDV infection or disease.

The gene encoding the MD06 polypeptide maps near the junction of the unique long (UL) region and the internal repeat structural element (IRL) within the MDV genome and encodes a polypeptide of about 290 amino acids in length, corresponding with a calculated molecular weight of 32 kDa.

"Nucleic acid sequence" as used herein refers to a polymeric form of nucleotides of any length, both to ribonucleic acid sequences and to deoxyribonucleic acid sequences. In principle, this term refers to the primary structure of the molecule. Thus, this term includes double and single stranded DNA, as well as double and single stranded RNA, and modifications thereof.

In general, the term "polypeptide" refers to a molecular chain of amino acids with a biological activity, does not refer to a specific length of the product and if required can be modified in vivo or in vitro, for example by glycosylation, amidation, carboxylation or phosphorylation; thus inter alia, peptides, oligopeptides and proteins are included.

The term "polypeptide having one or more immunogenic determinants of an MDV protein" refers to a polypeptide having one or more epitopes capable of eliciting an immune response in poultry against MDV infection or disease.

Also included within the scope of the present invention are nucleic acid sequences encoding a functional variant of the polypeptide shown in SEQ ID NO: 2. These functional variants are polypeptides having an amino acid sequance derived from the amino acid sequence specifically disclosed in SEQ ID NO: 2 but retain one or more immunogenic determinants of the MDV protein, i.e. said variants having one or more epitopes capable of eliciting an immune response in poultry against MDV infection or disease.

It will be understood that for the particular polypeptide embraced herein derived from the GA strain of serotype 1, natural variations can exist between individual viruses or strains of Marek's disease viruses. These variations may be demonstrated by (an) amino acid difference(s) in the overall sequence or by deletions, substitutions, insertions, inversions or additions of (an) amino acid(s) in said sequence. Amino acid substitutions from which can be expected that they do not essentially alter biological and immunological activities, have been described. Amino acid replacements between related amino acids or replacements which have occurred frequently in evolution are, inter alia Ser/Ala, Ser/Gly, Asp/Gly, Asp/Asn, Ile/Val (see Dayhof, M. D., Atlas of protein sequence and structure, Nat. Biomed. Res. Found., Washington D.C., 1978, vol. 5, suppl. 3). Based on this information Lipman and Pearson developed a method for rapid and sensitive protein comparison (Science 227, 1435–1441, 1985) and determining the functional similarity between homologous polypeptides. Nucleic acid sequences encoding such homologous functional variants are included within the scope of this invention. Moreover, the potential exists to use recombinant DNA technology for the preparation of nucleic acid sequences encoding these various functional variants.

Nucleic acid sequences according to the invention may be derived from isolates of MDV strains such as GA, JM, HPRS-16, Conn A, RB-IB, CVI-988 or Md 11, the GA strain (Eidson and Schnitte, Avian Diseases 12, 467, 1968) being the most preferred strain.

In addition nucleic acid sequences encoding the MD06 polypeptide or functional variants thereof as mentioned above can also be derived from MDV strains belonging to serotype 2 or serotype 3, e.g. HN, HPRS-24, SB-1 or FC126.

The information provided in SEQ ID NO: 1 and 2 allows a person skilled in the art to isolate and identify the nucleic acid sequences encoding the various functional variant polypeptides mentioned-above having corresponding immunological characteristics with the MD06 MDV protein specifically disclosed herein. The generally applied Southern blotting technique or colony hybridization can be used for that purpose (Experiments in Molecular Biology, ed. R. J. Slater, Clifton, U.S.A., 1986; Singer-Sam, J. et al., Proc. Natl. Acad. Sci. 80, 802–806, 1983; Maniatis T. et al., Molecular Cloning, A laboratory Manual, second edition, Cold Spring Harbor Laboratory Press, USA, 1989). For example, restriction enzyme digested DNA fragments derived from a specific MDV strain is electrophoresed and transferred, or "blotted" thereafter onto a piece of nitrocellulose filter. It is now possible to identify the nucleic sequences encoding the functional variant polypeptides on the filter by hybridization to a defined labelled DNA or "probe" back translated from the amino acid sequence shown in SEQ ID NO: 2, under specific conditions of salt concentration and temperature that allow hybridization of the probe to any homologous DNA sequences present on the filter. After washing the filter, hybridized material may be detected by autoradiography. Once having identified the relevant sequence, DNA fragments that encode a functionally variant polypeptide to the polypeptide disclosed in SEQ ID NO: 2 can now be recovered after agarose gel electrophoresis.

In another way MDV cDNA may be cloned into a $\lambda$ gt11 phage as described by Huynh et al. (In: D. Glover (ed.), DNA Cloning: A Practical Approach, IRL Press Oxford, 49–78, 1985) and expressed into a bacterial host. Recombinant phages can then be screened with polyclonal serum raised against the purified MD06 MDV protein disclosed in SEQ ID NO:2, determining the presence of corresponding immunological regions of the variant polypeptide. Above mentioned procedure is outlined in detail in Example 1. The production of the polyclonal serum to be used herein elicited against the MD06 MDV protein is described below.

A nucleic acid sequence according to the invention may be isolated from a particular MDV strain and multiplied by recombinant DNA techniques including polymerase chain reaction (PCR) technology or may be chemically synthesized in vitro by techniques known in the art.

A preferred nucleic acid sequence according to the invention is characterized in that said sequence contains at least part of the DNA sequence disclosed in SEQ ID NO:1.

As is well known in the art, the degeneracy of the genetic code permits substitution of bases in a codon resulting in an other codon but still coding for the same amino acid, e.g. the codon for the amino acid glutamic acid is both GAT and GAA. Consequently, it is clear that for the expression of a polypeptide with the amino acid sequence shown in SEQ ID NO: 2 use can be made of a variant nucleic acid sequence with such an alternative codon composition different from the nucleic acid sequence shown in SEQ ID NO:1.

Furthermore, also fragments of the nucleic acid sequences encoding the specifically disclosed MD06 MDV protein or functional variants thereof as mentioned above are included in the present invention.

The term "fragment" as used herein means a DNA or amino acid sequence comprising a subsequence of the nucleic acid sequence or polypeptide of the invention. Said fragment is or encodes a polypeptide having one or more immunogenic determinants of the MD06 MDV protein, i.e. has one or more epitopes of the MD06 protein which are capable of eliciting an immune response in poultry. Methods for determining usable polypeptide fragments are outlined below. Fragments can inter alia be produced by enzymatic cleavage of precursor molecules, using restriction endonucleases for the DNA and proteases for the polypeptides. Other methods include chemical synthesis of the fragments or the expression of polypeptide fragments by DNA fragments.

All modifications resulting in the above-mentioned functional variants of the specifically exemplified polypeptide are included within the scope of the present invention for as long as the resulting polypeptides retain one or more immunogenic determinants of the MD06 MDV protein.

A nucleic acid sequence according to the present invention can be ligated to various replication effecting DNA sequences with which it is not associated or linked in nature resulting in a so called recombinant vector molecule which can be used for the transformation of a suitable host. Useful recombinant vector molecules, are preferably derived from, for example plasmids, bacteriophages, cosmids or viruses.

Specific vectors or cloning vehicles which can be used to clone nucleic acid sequences according to the invention are known in the art and include inter alia plasmid vectors such as pBR322, the various pUC, pGEM and Bluescript plasmids, bacteriophages, e.g. λgt-Wes-λB, Charon 28 and the M13 derived phages or viral vectors such as SV40, adenovirus or polyoma virus (see also Rodriquez, R. L. and D. T. Denhardt, ed., Vectors: A survey of molecular cloning vectors and their uses, Butterworths, 1988; Lenstra, J. A. et al., Arch. Virol. 110, 1–24, 1990). The methods to be used for the construction of a recombinant vector molecule according to the invention are known to those of ordinary skill in the art and are inter alia set forth in Maniatis, T. et al. (Molecular Cloning A Laboratory Manual, second edition; Cold Spring Harbor Laboratory, 1989).

For example, the insertion of the nucleic acid sequence according to the invention into a cloning vector can easily be achieved when both the genes and the desired cloning vehicle have been cut with the same restriction enzyme(s) as complementary DNA termini are thereby produced.

Alternatively, it may be necessary to modify the restriction sites that are produced into blunt ends either by digesting the single-stranded DNA or by filling in the single-stranded termini with an appropriate DNA polymerase. Subsequently, blunt end ligation with an enzyme such as T4 DNA ligase may be carried out.

If desired, any restriction site may be produced by ligating linkers onto the DNA termini. Such linkers may comprise specific oligonucleotide sequences that encode restriction site sequences. The restriction enzyme cleaved vector and nucleic acid sequence may also be modified by homopolymeric tailing.

"Transformation", as used herein, refers to the introduction of a heterologous nucleic acid sequence into a host cell, irrespective of the method used, for example direct uptake or transduction. The heterologous nucleic acid sequence may be maintained through autonomous replication or alternatively, may be integrated into the host genome. If desired, the recombinant vector molecules are provided with appropriate control sequences compatible with the designated host which can regulate the expression of the inserted nucleic acid sequence. In addition to microorganisms, culture of cells derived from multicellular organisms may also be used as hosts.

The recombinant vector molecules according to the invention preferably contain one or more marker activities that may be used to select for desired transformants, such as ampicillin and tetracycline resistance in pBR322, ampicillin resistance and β-galactosidase activity in pUC8.

A suitable host cell is a pro- or eukaryotic cell which can be transformed by a nucleic acid sequence encoding a polypeptide or by a recombinant vector molecule comprising such a nucleic acid sequence and which can if desired be used to express said polypeptide encoded by said nucleic acid sequence. The host cell can be of prokaryotic origin, e.g. bacteria such as *Escherichia coli*, *Bacillus subtilis* and *Pseudomonas species*; or of eukaryotic origin such as yeasts, e.g. *Saccharomyces cerevisiae* or higher eukaryotic cells such as insect, plant or mammalian cells, including HeLa cells and Chinese hamster ovary (CHO) cells. Insect cells include the Sf9 cell line of *Spodoptera frugiperda* (Luckow et al., Bio-technology 6, 47–55, 1988). Information with respect to the cloning and expression of the nucleic acid sequence of the present invention in eukaryotic cloning systems can be found in Esser, K. et al. (Plasmids of Eukaryotes, Springer-Verlag, 1986).

In general, prokaryotes are preferred for cloning of DNA sequences in constructing the vectors useful in the invention.

For example *E. coli* K12 and derivative strains such as DH5α or JM101 are particularly useful.

For expression, nucleic acid sequences of the present invention are introduced into an expression vector, i.e. said sequences are operably linked to expression control sequences. Such control sequences may comprise promoters, enhancers, operators, inducers, ribosome binding sites etc. Therefore, the present invention provides a recombinant vector molecule comprising a nucleic acid sequence encoding the MD06 MDV protein operably linked to expression control sequences, capable of expressing the DNA sequences contained therein in (a) transformed host cell(s).

It should, of course, be understood that the nucleotide sequences inserted at the selected site of the cloning vector may include nucleotides which are not part of the actual structural gene for the desired polypeptide or may include only a fragment of the complete structural gene for the desired protein as long as transformed host will produce a polypeptide having at least one or more immunogenic determinants of the MD06 MDV protein.

When the host cells are bacteria, illustrative useful expression control sequences include the Trp promoter and operator (Goeddel, et al., Nucl. Acids Res. 8, 4057, 1980); the lac promoter and operator (Chang, et al., Nature 275, 615, 1978); the outer membrane protein promoter (Nakamura, K. and Inouge, M., EMBO J. 12, 771–775, 1982); the bacteriophage λ promoters and operators (Remaut, E. et al., Nucl. Acids Res. 11, 4677–4688, 1983); the α-amylase (B. subtilis) promoter and operator, termination sequence and other expression enhancement and control sequences compatible with the selected host cell. When the host cell is yeast, illustrative useful expression control sequences include, e.g., α-mating factor. For insect cells the polyhedrin or p10 promoters of baculoviruses can be used (Smith, G. E. et al., Mol. Cell. Biol. 3, 2156–65, 1983). When the host cell is of mammalian origin illustrative useful expression control sequences include, e.g., the SV40 promoter (Berman, P. W. et el., Science 222, 524–527, 1983) or, e.g. the metallothionein promoter (Brinster, R. L., Nature 296, 39–42, 1982) or a heat shock promoter (Voellmy et al., Proc. Natl. Acad. Sci. USA 82, 4949–53, 1985). Alternatively, also expression control sequences present in MDV, in particular those regulating the expression of the MD06 protein may be applied. For maximizing gene expression, see also Roberts and Lauer (Methods in Enzymology 68,473, 1979).

Therefore, the invention also comprises (a) host cell(s) transformed with a nucleic acid sequence or recombinant expression vector molecule described above, capable of producing the MD06 MDV protein by expression of the nucleic acid sequence.

The present invention also provides a purified polypeptide having one or more immunogenic determinants of a MD06 MDV protein having an amino acid sequence shown in SEQ ID NO:2, or a functional variant thereof, essentially free from the whole virus or other protein with which it is ordinarily associated.

It will be understood that derivatives of said amino acid sequences displaying the same immunological properties in essence, i.e. functional variants, are also within the scope of the present invention.

Functional variants of the MD06 polypeptide disclosed herein include the corresponding polypeptides present in viruses of other strains of MD serotype 1 (or in viruses of strains belonging to serotype 2 or 3). Said equivalents can be produced through the expression of the genes encoding said equivalents, the genes being identified and isolated making use of the information provided herein as described above.

In addition a polypeptide which can be used for immunization of poultry against MDV infection or disease or for diagnostic purposes substantially comprising an immunogenic fragment of the MD06 MDV protein is included in the present invention. Various methods are known for detecting such usable polypeptide fragments within a amino acid sequence.

Suitable immunochemically active immunogenic fragments of a polypeptide according to the invention containing (an) epitope(s) can be found by means of the method described in Patent Application WO 86/06487, Geysen, H. M. et al. (Prod. Natl. Acad. Sci. 81, 3998–4002, 1984), Geysen, H. M. et al. (J. Immunol. Meth. 102, 259–274, 1987) based on the so-called pep-scan method, wherein a series of partially overlapping polypeptides corresponding with partial sequences of the complete polypeptide under consideration, are synthesized and their reactivity with antibodies is investigated.

In addition, a number of regions of the polypeptide, with the stated amino acid sequence, can be designated epitopes on the basis of theoretical considerations and structural agreement with epitopes which are now known. The determination of these regions is based on a combination of the hydrophilicity criteria according to Hopp and Woods (Proc. Natl. Acad. Sci. 78, 3824–3828, 1981) and the secondary structure aspects according to Chou and Fasman (Advances in Enzymology 47, 45–148, 1987).

T-cell epitopes which may be necessary can likewise be derived on theoretical grounds with the aid of Berzofsky's amphiphilicity criterion (Science 235, 1059–62, 1987).

In another embodiment of the invention a polypeptide having an amino acid sequence encoded by a nucleic acid sequence mentioned above is used.

Immunization of poultry against MDV infection or disease can, for example be achieved by administering to the animals a polypeptide according to the invention in an immunologically relevant context as a so-called subunit vaccine. The subunit vaccine according to the invention may comprise a polypeptide in a pure form, optionally in the presence of a pharmaceutically acceptable carrier. The polypeptide can optionally be covalently bonded to a non-related protein, which, for example can be of advantage in the purification of the fusion product. Examples are β-galactosidase, protein A, prochymosine, blood clotting factor Xa, etc.

In some cases the ability to raise neutralizing antibodies against these polypeptides per se may be low. Small fragments are preferably conjugated to carrier molecules in order to raise their immunogenicity. Suitable carriers for this purpose are macromolecules, such as natural polymers (proteins like key hole limpet haemocyanin, albumin, toxins), synthetic polymers like polyamino acids (polylysine, polyalanine), or micelles of amphiphilic compounds like saponins. Alternatively these fragments may be provided as polymers thereof, preferably linear polymers.

Polypeptides to be used in such subunit vaccines can be prepared by methods known in the art, e.g. by isolating said polypeptides from MDV, by recombinant DNA techniques or by chemical synthesis.

If required the polypeptides according to the invention to be used in a vaccine can be modified in vitro or in vivo, for example by glycosylation, amidation, carboxylation or phosphorylation.

An alternative to subunit vaccines are live vector vaccines. A nucleic acid sequence according to the invention is introduced by recombinant DNA techniques into a micro-organism (e.g. a bacterium or virus) in such a way that the recombinant micro-organism is still able to replicate thereby expressing a polypeptide coded by the inserted nucleic acid sequence and eliciting an immune response in the infected host animal.

A preferred embodiment of the present invention is a recombinant vector virus comprising a heterologous nucleic acid sequence described above, capable of expressing the DNA sequence in (a) host cell(s) or host animal infected with the recombinant vector virus. The term "heterologous" indicates that the nucleic acid sequence according to the invention is not normally present in nature in the vector virus or is not present in the same genetic context as in the naturally occurring vector virus.

Furthermore, the invention also comprises (a) host cell(s) or cell culture infected with the recombinant vector virus, capable of producing the MDV protein by expression of the nucleic acid sequence.

The well known technique of in vivo homologous recombination can be used to introduce a heterologous nucleic acid sequence, e.g. a nucleic acid sequence according to the invention into the genome of the vector virus.

First, a DNA fragment corresponding with an insertion region of the vector genome, i.e. a region which can be used for the incorporation of a heterologous sequence without disrupting essential functions of the vector such as those necessary for infection or replication, is inserted into a cloning vector according to standard recDNA techniques. Insertion-regions have been reported for a large number of micro-organisms (e.g. EP 80,806, EP 110,385, EP 83,286, EP 314,569, WO 88/02022 and WO88/07088).

Second, if desired, a deletion can be introduced into the insertion region present in the recombinant vector molecule obtained from the first step. This can be achieved for example by appropriate exonuclease III digestion or restriction enzyme treatment of the recombinant vector molecule from the first step.

Third, the heterologous nucleic acid sequence is inserted into the insertion-region present in the recombinant vector molecule of the first step or in place of the DNA deleted from said recombinant vector molecule. The insertion region DNA sequence should be of appropriate length as to allow homologous recombination with the vector genome to occur. Thereafter, suitable cells can be infected with wild-type vector virus or transformed with vector genomic DNA in the presence of the recombinant vector molecule containing the insertion flanked by appropriate vector DNA sequences whereby recombination occurs between the corresponding regions in the recombinant vector molecule and the vector genome. Recombinant vector progeny can now be produced in cell culture and can be selected for example genotypically or phenotypically, e.g. by hybridization, detecting enzyme activity encoded by a gene co-integrated along with the heterologous nucleic acid sequence, or detecting the antigenic heterologous polypeptide expressed by the recombinant vector immunologically.

Next, this recombinant micro-organism can be administered to the host animal for immunization after which it maintains itself for some time, or even replicates in the body of the inoculated animal, expressing in vivo a polypeptide coded for by the inserted nucleic acid sequence according to the invention resulting in the stimulation of the immune system of the inoculated animal. Suitable vectors for the incorporation of a nucleic acid sequence according to the invention can be derived from viruses such as (avian) poxviruses, e.g. vaccinia virus or fowl poxvirus (EP 314,569 and WO 88/02022), herpesviruses, for example vaccine strains of Marek's Disease viruses such as HVT (WO 88/07088) or MDV strains of serotype 1 or 2, adenovirus or influenzavirus, or bacteria such as *E. coli* or specific Salmonella species. These vectors can be designed in a way to obtain an efficient recognition of the polypeptide by the immune system of the host animal. In this context fusion of the said polypeptide with synthetic signal and anchor sequences or with an antigen from another viral or bacterial pathogen, e.g. the haemagglutinin-neuraminidase protein form Newcastle disease virus, are conceivable. It is also possible that the said immunogenic polypeptide, if desired as part of a larger whole, is released inside the animal to be immunized. In all of these cases it is also possible that one or more immunogenic products will find expression which generate protection against various pathogens and/or against various antigens of a given pathogen.

A vaccine according to the invention can be prepared by culturing a host cell infected with a recombinant vector virus comprising a nucleic acid sequence according to the invention, after which virus containing cells and/or recombinant vector viruses grown in the cells can be collected, optionally in a pure form. Another possibility to produce a vector vaccin is to incorporate a nucleic acid sequence according to the invention in an infectious bacteria or parasite and to culture such a modified infectious agent. After collection, optionally in a pure form, a vaccine, optionally in a lyophilized form, can be produced Host cells transformed with a recombinant vector molecule according to the invention can also be cultured under conditions which are favourable for the expression of a polypeptide coded by said nucleic acid sequence. Vaccines may be prepared using samples of the crude culture, host cell lysates or host cell extracts, although in another embodiment more purified polypeptides according to the invention are formed to a vaccine, depending on its intended use. In order to purify the polypeptides produced, host cells transformed with a recombinant vector according to the invention are cultured in an adequate volume and the polypeptides produced are isolated from such cells or from the medium if the protein is excreted. Polypeptides excreted into the medium can be isolated and purified by standard techniques, e.g. salt fractionation, centrifugation, ultrafiltration, chromatography, gel filtration or immuno affinity chromatography, whereas inter cellular polypeptides can be isolated by first collecting said cells, disrupting the cells, for example by sonication or by other mechanically disruptive means such as French press followed by separation of the polypeptides from the other inter cellular components and forming the polypeptides to a vaccine. Cell disruption could also be accomplished by chemical (e.g. EDTA treatment) or enzymatic means such as lysozyme digestion.

Antibodies or antiserum directed against a polypeptide according to the invention have potential use in passive immunotherapy, diagnostic immunoassays and generation of anti-idiotype antibodies.

The MD06 MDV protein as characterized above can be used to produce antibodies, both polyclonal, monospecific and monoclonal. If polyclonal antibodies are desired, techniques for producing and processing polyclonal sera are known in the art (e.g. Mayer and Walter, eds, Immunochemical Methods in Cell and Molecular Biology, Academic Press, London, 1987). In short, a selected mammal, e.g. rabbit is given (multiple) injections with above-mentioned immunogen, about 20 μg to about 80 μg of protein per immunization. Immunization are given with an acceptable adjuvant, generally equal volumes of immunogen and adjuvant. Acceptable adjuvants include Freund's complete, Freund's incomplete, alum-precipitate or water-in-oil emulsions, with Freund's complete adjuvant being preferred for the initial immunization. Freund's incomplete adjuvant is preferred for all booster immunizations. The initial immunization consists of the administration of about 1 ml of emulsion at multiple subcutaneous sites on the backs of the rabbits. Booster immunizations utilizing an equal volume of immunogen are given at about one month intervals and are continued until adequate levels of antibodies are present in an individual rabbits serum. Blood is collected and serum isolated by methods known in the art.

Monospecific antibodies to the immunogen are affinity purified from polyspecific antisera by a modification of the method of Hall et al. (Nature 311, 379–387 1984), prepared by immunizing rabbits as described above with the purified protein. Monospecific antibody as used herein is defined as a single antibody species or multiple antibody species with homogeneous binding characteristics for the relevant antigen. Homogeneous binding as used herein refers to the ability of the antibody species to bind to a specific antigen or epitope.

Monoclonal antibody reactive against the MD06 MDV immunogen can be prepared by immunizing inbred mice, preferably Balb/c with the appropriate protein. The mice are immunized intraperitoneally with about 100 ng to about 10 μg immunogen per 0.5 ml dosis in an equal volume of an acceptable adjuvant. Such acceptable adjuvants include Freund's complete, Freund's incomplete, alum-precipitate and water-in-oil emulsions. The mice are given intravenous booster immunizations of an equal amount of the immunogen without adjuvant at about days 14, 21 and 63 post primary immunization. At about day three after the final booster immunization individual mice are serologically tested for anti-immunogen antibodies. Spleen cells from antibody producing mice are isolated and fused with murine myeloma cells, such as SP-2/0 or the like, by techniques known in the art (Kohler and Milstein, Nature 256; 495–497, 1975). Hybridoma cells are selected by growth in hypoxanthine, thymidine and aminopterin in an appropriate cell culture medium such as Dulbecco's modified Eagle's medium (DMEM). Antibody producing hybridomas are cloned, preferably using the soft agar technique of MacPherson, (Soft Agar Techniques, Tissue Culture Methods and Applications, Kruse and Paterson, eds., Academic Press, 276, 1973), Discrete colonies are transferred into individual wells of culture plates for cultivation in an appropriate culture medium. Antibody producing cells are identified by screening with the appropriate immunogen. Immunogen positive hybridoma cells are maintained by techniques known in the art. Specific anti-monoclonal antibodies are produced by cultivating the hybridomas in vitro or preparing ascites fluid in mice following hybridoma injection by procedures known in the art.

Anti-idiotype antibodies are immunoglobulins which carry an "internal image" of the antigen of the pathogen against which protection is desired and can be used as an immunogen in a vaccine (Dreesman et al., J. Infect. Disease 151, 761, 1985). Techniques for raising anti-idiotype antibodies are known in the art (MacNamara et al., Science 226, 1325, 1984).

The vaccine according to the invention can be administered in a conventional active immunization scheme: single or repeated administration in a manner compatible with the dosage formulation and in such amount as will be prophylactically and/or therapeutically effective and immunogenic, i.e. the amount of immunizing antigen or recombinant micro-organism capable of expressing said antigen that will induce immunity in an animal against challenge by a virulent MDV. Immunity is defined as the induction of a higher level of protection in a population of animals after vaccination compared to an unvaccinated group.

For live viral vector vaccines the dose rate per animal may range from $1.10^2$–$1.10^6$ injectivity units.

A typical subunit vaccine according to the invention comprises 10 μg–1 mg of the polypeptide according to the invention.

The administration of the vaccine can be done, e.g. intradermally, subcutaneously, intramuscularly, intraperitonially, intravenously, orally or intranasally.

Additionally the vaccine may also contain an aqueous medium or a water containing suspension, often mixed with other constituents, e.g. in order to increase the activity and/or shelf life. These constituents may be salts, pH buffers, stabilizers (such as skimmed milk or casein hydrolysate), emulsifiers adjuvants to improve the immune response (e.g. oils, muramyl dipeptide, aluminiumhydroxide, saponin, polyanions and amphipatic substances) and preservatives.

It is clear that a vaccine according to the invention may also contain immunogens related to other pathogens of poultry or may contain nucleic acid sequences encoding these immunogens, like antigens of Infectious Bronchitis Virus (IBV), Newcastle Disease Virus (NDV), Infectious Bursal Disease Virus (IBDV) or Marek's Disease Virus different from those disclosed herein, to produce a multivalent vaccine.

The invention also relates to an "immunochemical reagent", which reagent comprises a polypeptide according to the invention.

The term "immunochemical reagent" signifies that the polypeptide according to the invention is bound to a suitable support or is provided with a labelling substance.

The supports which can be used are, for example, the inner wall of a microtest well or a cuvette, a tube or capillary, a membrane, filter, test strip or the surface of a particle such as, for example, a latex particle, an erythrocyte, a dye sol, a metal sol or metal compound as sol particle.

Labelling substances which can be used are, inter alia, a radioactive isotope, a fluorescent compound, an enzyme, a dye sol, metal sol or metal compound as sol particle.

A nucleic acid sequence according to the invention can also be used to design specific probes for hybridization experiments for the detection of MDV related nucleic acids in any kind of tissue.

The present invention also provides a test kit comprising said nucleic acid sequence useful for the diagnosis of MDV infection or disease.

The invention also relates to a test kit to be used in an immuno-assay, this test kit containing at least one immunochemical reagent according to the invention.

The immunochemical reaction which takes place using this test kit is preferably a sandwich reaction, an agglutination reaction, a competition reaction or an inhibition reaction.

For carrying out a sandwich reaction, the test kit can consist, for example, of a polypeptide according to the invention bound to a solid support, for example the inner wall of a microtest well, and either a labelled polypeptide according to the invention or a labelled anti-antibody.

EXAMPLE 1

Screening of bacterial expression libraries with convalescent chicken serum

The vectors used for establishment of the library have been λgt11 (Young, R. A. and Davis, R. W. Proc. Natl. Acad. Sci. 80, 1194–1198, 1983) and λEMBL-3. The genome of the λgt11 expression vector contains a functional LacZ gene encoding the enzyme β-galactosidase with a unique EcoRI restriction site near the carboxy terminus. Insertion of DNA fragments from the MDV genome at this site, potentially results in the expression of a protein consisting of an MDV specific polypeptide fused to a major part of the β-galactosidase. Libraries representing a complex range of DNA fragments can be screened at high density for recombinant clones producing a fusion protein which is recognized by an antibody probe such as the serum from MDV infected birds.

A library representing the genome of MDV strain GA consisted of about 100 independent λEMBL-3 recombinants containing an average insert size of about 18 kbp. These recombinants were selected by hybridizing a phage library, representing the total DNA content of MDV strain GA infected chicken embryo fibroblasts (CEF), with a probe consisting of a pool of BamHI plasmid clones containing MDV specific sequences (Fukuchi et al., J. Virol. 51, 102, 1984). DNA from the amplified GA-specific EMBL-3 library was fragmented by partial digestion with a mixture of the restriction enzymes AluI, RsaI and HaeIII. Fragments with a size between 0.5 and 4.0 kb were isolated, tailed with dG-residues and inserted by means of a synthetic adaptor into the unique EcoRI-site of the λgt10 vector (Le Bouc et al., FEBS lett. 196, 108, 1986; Huynh et al., in: Cloning Techniques, A Practical Approach, ed. Glover, D., 49–78, 1985) resulting in a library with an effective size of 4×104 pfu. Phages were amplified and purified on CsCl-gradients, DNA was extracted and inserts were recovered by restriction with EcoRI. Finally, these inserts were ligated into the EcoRI-site of the λgt11 vector and recombinant phages were screened with chicken serum against MDV.

This convalescent serum was obtained by infecting single-comb white leghorns (SPAFAS) with a virulent passage of the GA strain from MDV obtained from Dr. Calnek (Cornell University, N.Y., USA). Serum was collected over a 12 weeks period and samples were tested individually by indirect fluorescence for binding to MDV plaques in tissue cultures of chicken embryo fibroblasts (CEF).

Six of the sera were selected based on titre and specificity. A mixture of these samples was used in a 1:100 dilution to screen the λgt11 library on nitro-cellulose filters according to Young, R. A. et al. (Proc. Natl. Acad. Sci. U.S.A. 82, 2583, 1985). The second antibody for incubation of the filters was an alkaline phosphatase conjugated rabbit-anti-chicken serum (Sigma, St. Louis, USA) and positive signals were developed by the nitro blue tetrazolium/5-bromo-4-chloro-3-indolyl phosphate colour reaction (McGadey, Histochemie 23, 180, 1970). Series of candidates were selected and recombinants were plaque-purified until homogeneity.

A major group among these λgt11 candidates contained inserted sequences with strong similarities based on cross-hybridization experiments. One of them was selected and the DNA insert of about 500 bp was transferred to pGEM3Z (Promega, Madison, USA) resulting in plasmid pMD06.

EXAMPLE 2

Cloning and structural analysis of the gene encoding the MD06 antigen.

Figure 1:
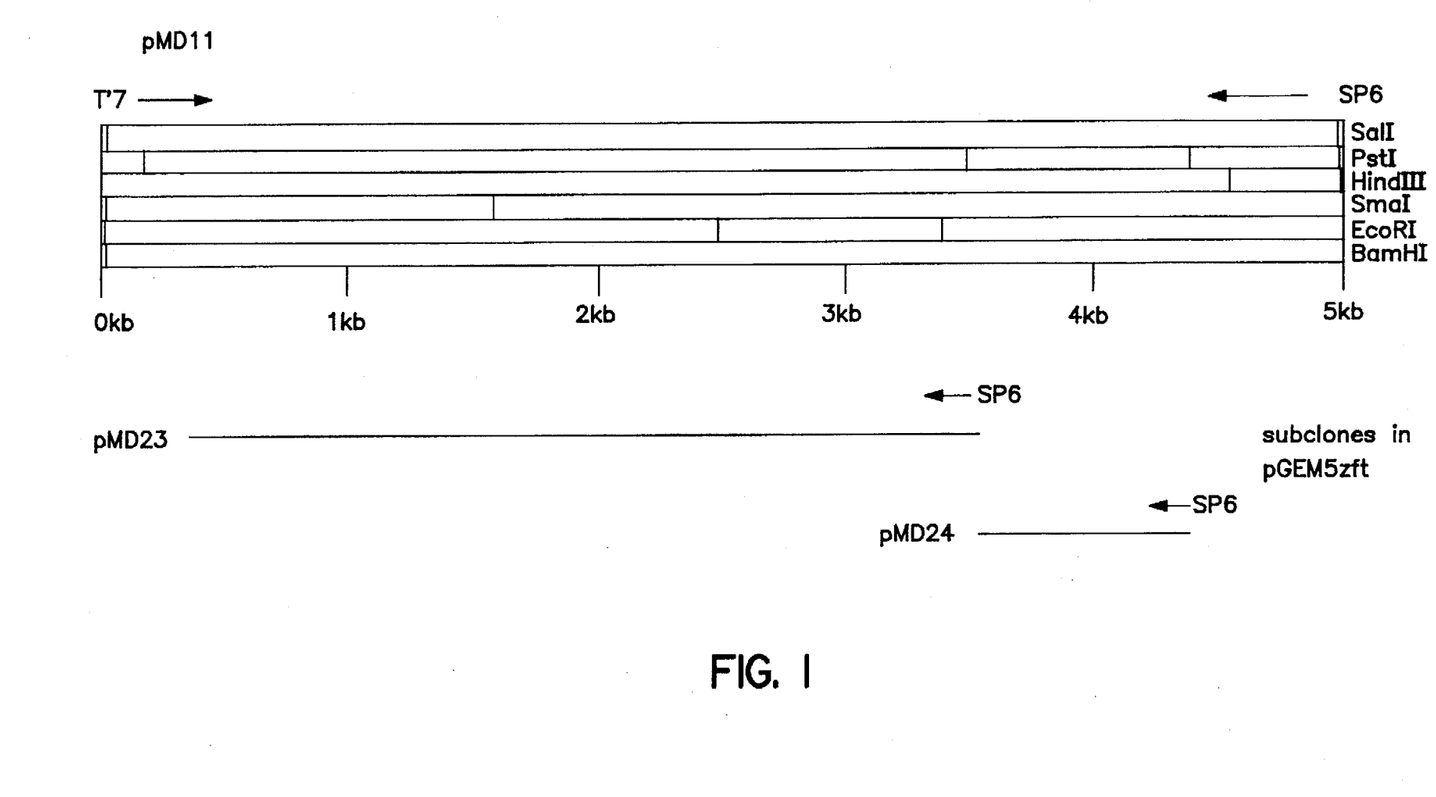

The previously established MDV strain GA-specific EMBL-3 library was screened on replica filters using the labelled insert from pMD06 as a probe. Positive signals were selected, plaque purified and DNA was extracted from amplified phage preparations. One of the candidates, designated XGA08, was analyzed by restriction mapping and southern blot hybridization using the labelled insert from pMD06 as a probe. Strong hybridization was obtained to a 5.0 kb SalI fragment present in the 17 kb insert of λGA08. Subcloning of this particular fragment in pGEM3Z resulted in pMD11, the restriction map of which is shown in FIG. 1. Relevant fragments from pMD11 were obtained by subcloning two PstI fragments of 3.3 and 0.9 kb in pGEM5Z resulting in pMD23 and pMD24 respectively. Nucleotide sequence analysis was performed in the region of the 0.9 kb EcoRI restriction fragment shown in FIG. 1.

Both strands were analyzed based on progressively deleted subclones generated by endonuclease III treatment as described by Henikoff (Gene 28, 357, 1984) on either plasmid pMD11 or pMD23. All reactions were performed on double stranded DNA preparations using a T7 polymerase sequencing kit (Pharmacia Inc., Piscataway, N.J.). Gel readings were assembled using the shotgun handler from a Gene-Master workstation (Bio-Rad, Richmond, Calif.). The result of this analysis is shown in SEQ ID NO: 1 and revealed an open reading frame of 830 nucleotides essentially encoding the MD06 antigen of about 290 amino acids of which the primary structure is shown in SEQ ID NO:2.

EXAMPLE 3

Expression of antigen MD06 as a fusion polypeptide with the heamagglutinin-neuramidase (HN) protein from Newcastle disease virus (NDV) using herpesvirus of turkey (HVT) as a live viral vector.

The expression of the antigen in a vector organism can be envisaged such that exposure on the cell surface increases the efficiency with which the host immune system recognizes the relevant antigenic epitopes. An example of such a carrier protein is HN from NDV. The gene encoding this protein can be inserted in the genome of an arian viral vector e.g. HVT, in such a way that HN is efficiently synthesized after infection of a cell with the recombinant virus. The DNA fragment encoding a substantial part of MD06 is subsequently integrated at a suitable position within the coding region for HN such that the proper orientation and reading frame is respected. The fusion polypeptide now synthesized by the infected cell can be directed to the outer surface and correctly anchored in the plasma membrane through the amino terminal sequence of HN.

A. Vector plasmid mediating the integration of genes into the genome of HVT.

Figure 2:
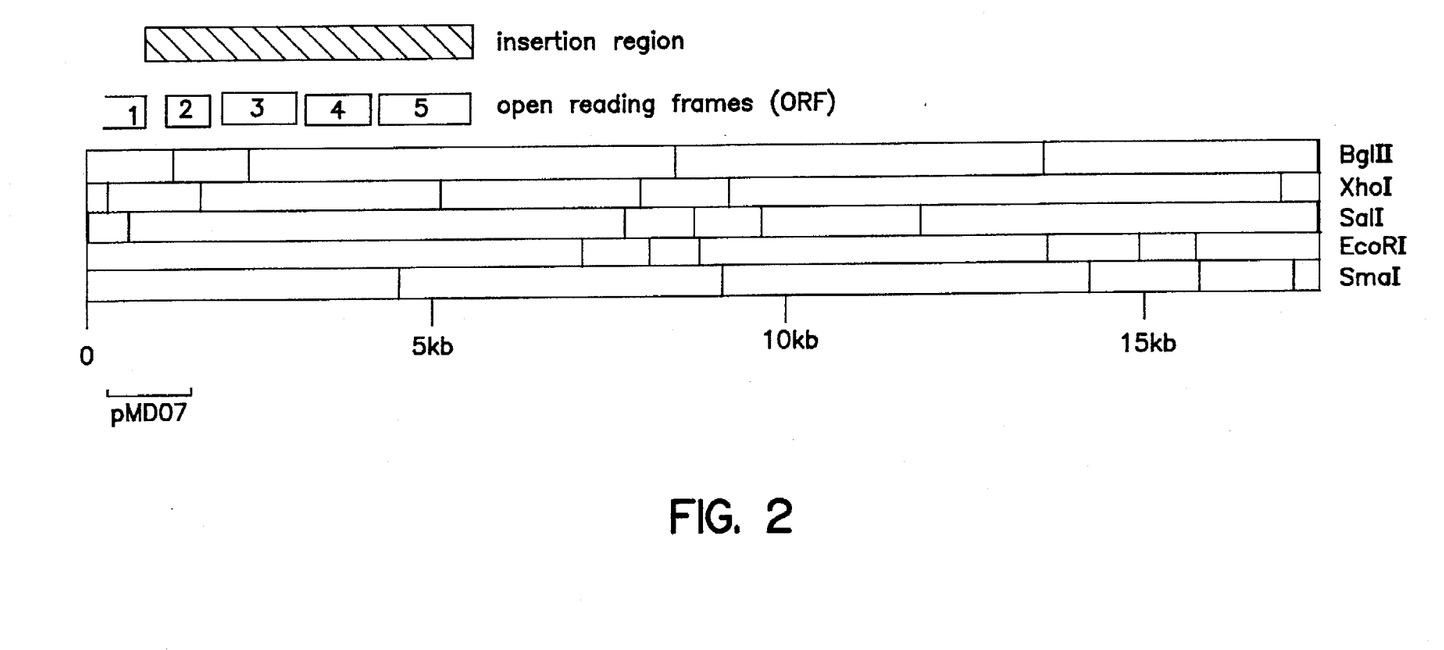
Figure 3:
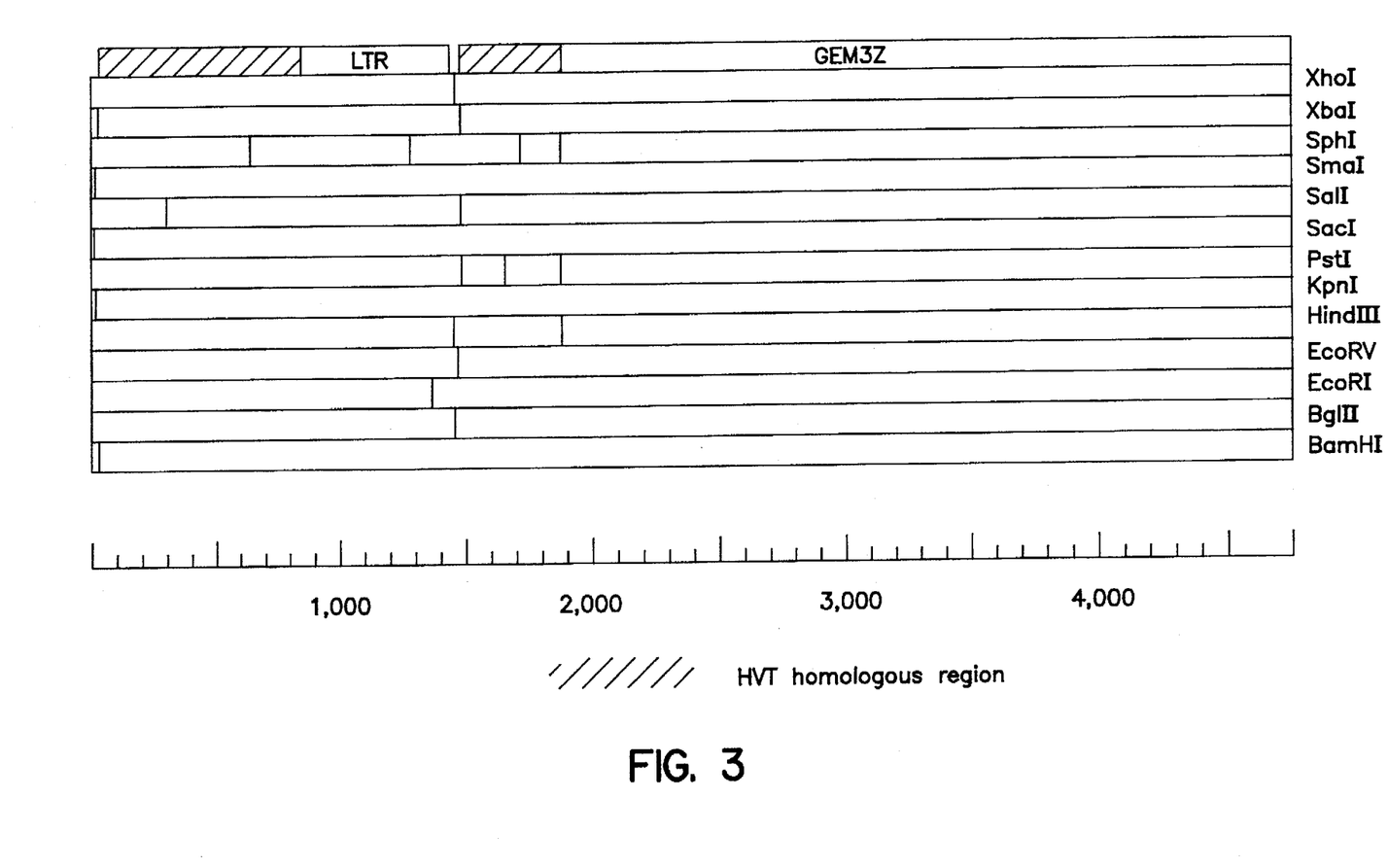

Based on the genome structure of HVT as published by Igarashi, T.. et al. (Virology 157, 351, 1987) a region in the unique-short sequence element (Us) of the virus was selected for the insertion of foreign genes. The corresponding DNA fragment was screened from a λEMBL3 library constructed by partially digesting total DNA from HVT infected CEF. The insert of one of the λ-isolates, characterized by the absence of any BamHI restriction site, was denominated λHVT04. The sequence present in the 17.5 kb inserted fragment represented a major part of the Us region including part of the inverted repeat structure (Igarashi, T. et al., 1987, ibid). One of the 1.2 kb XhoI restriction fragments from λHVT04 was subcloned in pGEM3Z digested with Sal I resulting in plasmid pMD07 which contained a unique BglII site available for insertion of DNA fragments (FIG. 2). A strong promoter which could direct the expression of foreign genes after their insertion into the genome of the HVT virus was selected from the LTR sequence of Rous Sarcoma Virus (RSV). The promoter has been mapped on a 580 bp NdeI/HindIII restriction fragment from pRSVcat (Gorman et al., Proc. Natl. Acad. Sci. 79, 6777, 1982) and was inserted between the HindIII and PstI sites of pGEM3Z (Promega) by means of double stranded synthetic linkers on both sides of the fragment. The connection between the HindIII site from the vector pGEM3Z and the NdeI site of the RSV fragment carrying the LTR-promoter was made with a 30 bp linker containing cohesive ends compatible with HindIII on one and NdeI on the other site. However, after ligation both restriction sites are not restored due to deliberate modifications in the outer nucleotides of the six basepair recognition sequence. In addition to the removal of these two sites, a new restriction site (BamHI) present within the linker itself was created at the corresponding position. A second 20 bp linker was synthesized which connected the HindIII site from the LTR fragment to the PstI site from pGEM3Z, in this case without destruction of the recognition sequence on either of the ends and adding the three convenient unique restriction sites BglII, XhoI and EcoRV, to those already present in the polylinker of pGEM3Z, e.g. PstI, SalI, XhoI and BamHI. The resulting derivative of pGEM3Z, designated pVEC01, therefore contains a 650 bp restriction fragment carrying the LTR promoter sequence immediately followed by seven restriction sites available for the insertion of foreign genes. The 650 bp fragment is flanked on either end by a BamHI restriction site and has been transferred as such to the unique BglII site present in the 1,2 kb HVT insert from pMD07. The cohesive ends generated by these two restriction enzymes are compatible but ligation does not restore either of the original recognition sequences for BglII or BamHI. One of the resulting constructs, carrying the LTR in the orientation towards the TRs, was designated pVEC04 and checked by restriction mapping (FIG. 3). The structure of this universal HVT recombination vector allows the insertion of foreign genes immediately downstream of the LTR promoter and subsequent integration of the complete expression cassette into the HVT genome by in vivo recombination. The positions of the different restriction sites downstream of the LTR in particular those for the enzymes BglII, XhoI and EcoRV are designed in such a way that even multiple gene insertion can be envisaged.

B. Insertion of the HN-gene from MDV into pVEC04.

Figure 4:
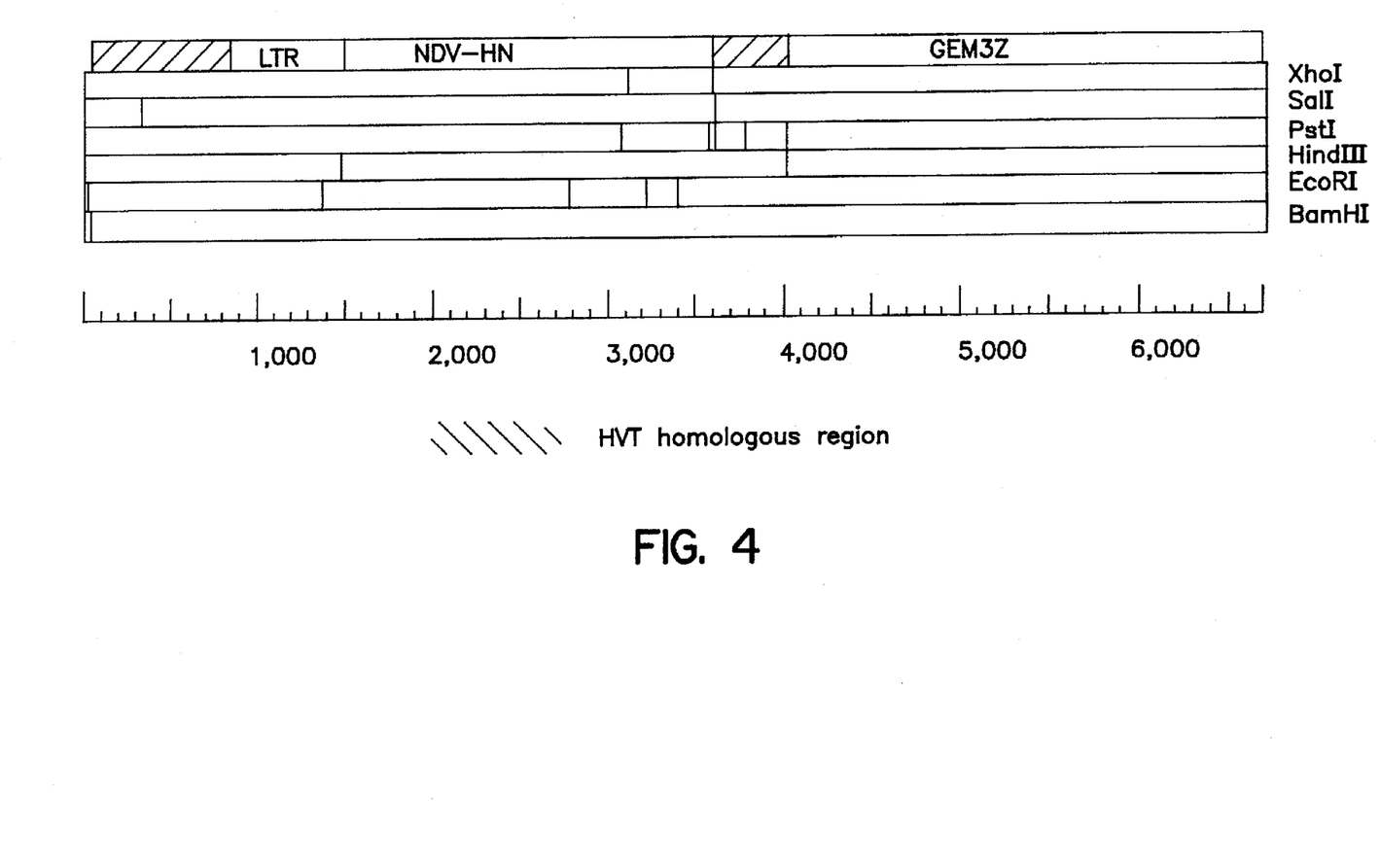

The gene encoding HN was isolated from a cDNA library of NDV strain Clone 30 (Intervet Int., Holland). Genomic RNA was prepared from virus grown on embryonated eggs and first strand cDNA synthesis was performed with reverse transcriptase using a random 10-base oligomer to prime the reaction. The DNA fragment flanked by BamHI restriction sites and encoding the complete HN protein was cloned in pGEM4Z (Promega, Madison, USA) and the resulting plasmid was designated pNDV03. Subsequent transfer of the 2.1 kb BamHI fragment into the BglII site of the recombination vector pVEC04 resulted in pNDV05. Correct orientation of the inserted gene relative to the LTR promoter was verified by restriction analysis based on the physical map as shown in FIG. 4.

C. Construction of a fusion between the gene encoding MDV antigen MD06 and the HN from NDV.

Figure 5:
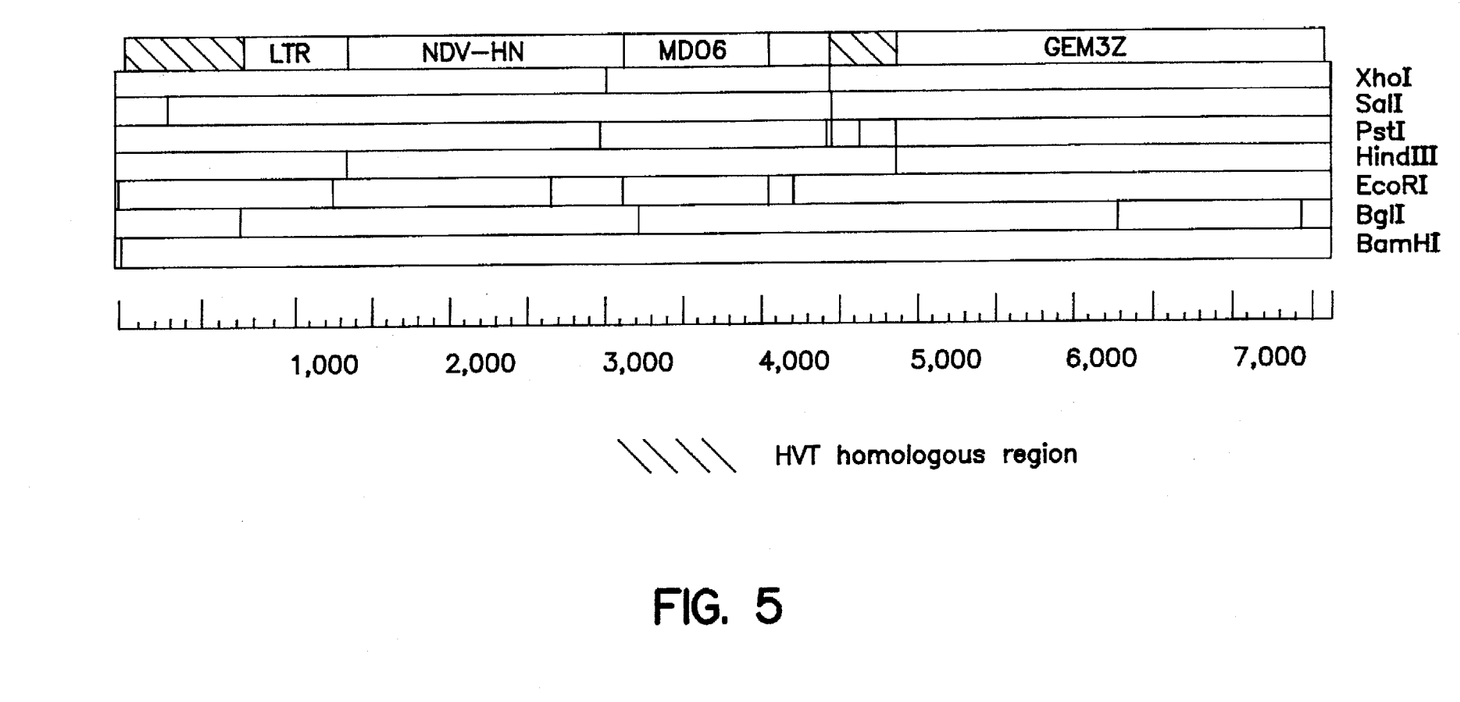

Examination of the sequence of the coding region from HN reveales that the GAA-codon of the EcoRI restriction site present in the 3' terminal part of the gene has the same reading frame as the second codon of the gene encoding MD06 as show in SEQ ID:1. Correctly orientated integration of a 0.9 kb EcoRI fragment derived from pMD11 or pMD23 at the relevant EcoRI restriction site in pNDV05 results in synthesis of a polypeptide comprising almost the entire HN protein fused to the complete MD06 antigen. This particular plasmid construction derived from pNDV05 is designated pNDV10 and the restriction map is shown in FIG. 5.

Additional integration of a marker gene can be envisaged at the EcoRV site present at the 3' end of the gene encoding the fusion polypeptide. The presence of a marker gene such as the lacZ gene from *E. coli* facilitates the detection of recombinant HVT virus expressing both β-galactosidase activity and the fusion polypeptide of interest.

D. Insertion of genes into the genome of HVT.

DNA from plasmid pNDV10 is introduced together with total DNA prepared from HVT infected cells into CEF by a method based on the calcium phosphate DNA precipitation according to Graham and v.d. Eb (Virology 52, 456, 1973) with modifications described by Morgan et al. (Avian Diseases 34, 345, 1990). Two micrograms of plasmid DNA from the constructs are mixed with 15 µg of DNA from HVT infected cells in a final volume of 560 µl H2O and added to 750 µl of HBSP (20 mM KCl, 560 mM NaCl, 24 mM glucose, 3 mM Na2HPO4, 100 mM HEPES, pH 7,0). Precipitates are formed by gradually adding 190 µl of 1M $CaCl_2$ solution and incubating the mixtures at room-temperature for 30 minutes. In the meantime, 15 ml of a suspension of secondary CEF from 10 day old embryos in medium 6/B8, for which the composition is based on Glasgow's modification of Eagle's Minimal Essential Medium supplemented with 2% of foetal calf serum, were seeded in 80 $cm^2$ dishes at a density of 5×105 cells per ml. Calcium phosphate precipitated DNA is gently added to the cell suspension and dishes are incubated at 37° C. in a humidified incubator containing 5% CO2 in air. After 5 hours, medium is removed and 10 ml of solution containing equal volumes of HBSP and 30% glycerol is layered onto the cells. After a one to two minute incubation, the solution is removed, cells are washed with medium 6/B8 and dishes are incubated with fresh medium for 3 to 5 days until viral CPE develops. Detection of HVT recombinants expressing the MD06 antigen fused to the HN of NDV is done by immunofluorescence staining using specific mono- or polyvalent sera against the MDV antigens or the HN protein from NDV.

BRIEF DESCRIPTION OF THE DRAWINGS

FIG. 1

Restriction enzyme map of pMD11 with the position of the 0.9 Kb EcoRI-fragment. This fragment showed strong hybridization to the insert of pMD06.

FIG. 2

Restriction enzyme map of a DNA fragment essentially corresponding to the Us region of the HVT genome. The relative position of the insertion-region consisting of four open reading frames and non-coding sequences in between is indicated.

FIG. 3

Restriction enzyme map of pVEC04 showing the LTR-promoter inserted into the unique BglII site of the 1,2 kb XhoI HVT fragment from pMD07.

FIG. 4

Restriction map of pNDV05. Plasmid contains NDV-HN gene flanked by BamHI sites inserted into BglII site of pVEC04 (see FIG. 3).

FIG. 5

Restriction map of pNDV10. Plasmid is derived from pNDV05 by inserting a 0.9 kb EcoRI fragment essentially encoding the MD06 polypeptide at the EcoRI site positioned at about 3200 bases of pNDV05 (see FIG. 4).

---

We claim:

1. An isolated polypeptide comprising at least one immunogenic determinant of a MD06 MDV protein having an amino acid sequence shown in SEQ ID NO:2 or a functional variant thereof.

2. A vaccine for the protection of poultry against Marek's disease comprising an immunologically effective amount of a polypeptide according to claim 1, together with a pharmaceutically acceptable carrier.

3. An immunochemical reagent comprising a polypeptide according to claim 1 presenting an immunogenic determinant of MDV.

4. A process for the preparation of a MDV vaccine comprising formulating a pharmaceutical preparation with immunizing activity comprising the polypeptide according to claim 1 and a pharmaceutically acceptable carrier.

5. A process for the protection of poultry against MDV infection or disease comprising administering an effective amount of a vaccine according to claim 2 to an animal.

6. An isolated MDV polypeptide comprising an immunogenic determinant encoded by a nucleic sequence comprising at least part of the DNA sequence shown in SEQ ID NO:1.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 975 base pairs
        ( B ) TYPE: nucleic acid
        ( C ) STRANDEDNESS: double
        ( D ) TOPOLOGY: linear     ( i i ) MOLECULE TYPE: DNA (genomic)

( v i ) ORIGINAL SOURCE:
        ( A ) ORGANISM: Mareks Disease Virus
        ( B ) STRAIN: Georgia (GA)

( v i i ) IMMEDIATE SOURCE:
        ( B ) CLONE: pMD11

( i x ) FEATURE:
        ( A ) NAME/KEY: CDS
        ( B ) LOCATION: 46..918
        ( D ) OTHER INFORMATION: /label=MD06_antigen     ( x i ) SEQUENCE DESCRIPTION: SEQ ID NO:1:

```
ACCGCACGCT TGCTCGTCC  CCGCGTGCAA GATCGGCAGG GGCTG ATG GAA TTC            54
                                                  Met Glu Phe
                                                   1

GAA GCA GAA CAC GAA GGG CTG ACG GCG TCT TGG GTC GCC CCC GCT CCC         102
Glu Ala Glu His Glu Gly Leu Thr Ala Ser Trp Val Ala Pro Ala Pro
  5              10                  15
```

| | | | | | | | | | | | | | | | | |
|---|---|---|---|---|---|---|---|---|---|---|---|---|---|---|---|---|
|CAG|GGT|GGA|AAA|GGG|GCG|GAG|GGC|CGC|GCA|GGG|GTC|GCC|GAC|GAG|GCA|150|
|Gln|Gly|Gly|Lys|Gly|Ala|Glu|Gly|Arg|Ala|Gly|Val|Ala|Asp|Glu|Ala||
|20|||||25|||||30|||||35||

|GGG|CAT|GGG|AAA|ACA|GAA|GCG|GAA|TGC|GCC|GAG|GAC|GGC|GAG|AAA|TGC|198|
|Gly|His|Gly|Lys|Thr|Glu|Ala|Glu|Cys|Ala|Glu|Asp|Gly|Glu|Lys|Cys||
||||40|||||45|||||50|||

|GGG|GAC|GCC|GAG|ATG|AGC|GCT|TTG|GAT|CGG|GTC|CAG|AGG|GAC|CGG|TGG|246|
|Gly|Asp|Ala|Glu|Met|Ser|Ala|Leu|Asp|Arg|Val|Gln|Arg|Asp|Arg|Trp||
||||55|||||60|||||65|||

|AGA|TTC|AGT|TCT|CCG|CCC|CCT|CAC|TCT|GGA|GTC|ACG|GGG|AAG|GGG|GCT|294|
|Arg|Phe|Ser|Ser|Pro|Pro|Pro|His|Ser|Gly|Val|Thr|Gly|Lys|Gly|Ala||
|||70|||||75|||||80||||

|ATT|CCA|ATA|AAG|GGT|GAT|GGG|AAG|GCG|ATA|GAA|TGC|CAG|GAG|CTA|ACC|342|
|Ile|Pro|Ile|Lys|Gly|Asp|Gly|Lys|Ala|Ile|Glu|Cys|Gln|Glu|Leu|Thr||
|||85|||||90|||||95||||

|GGA|GAG|GGA|GAG|TGG|CTG|TCA|CAG|TGG|GAG|GAG|CTA|CCG|CCT|GAG|CCC|390|
|Gly|Glu|Gly|Glu|Trp|Leu|Ser|Gln|Trp|Glu|Glu|Leu|Pro|Pro|Glu|Pro||
|100||||||105|||||110||||115||

|CGG|AGG|TCA|GGG|AAT|GAA|CAT|CTT|GAC|GAA|AGT|CGG|TAT|GCG|AAA|CAA|438|
|Arg|Arg|Ser|Gly|Asn|Glu|His|Leu|Asp|Glu|Ser|Arg|Tyr|Ala|Lys|Gln||
||||120|||||125|||||130|||

|ACC|GAA|AGG|GGT|AGC|TCT|ACG|GGG|AAA|GAA|GAG|GGA|GAT|GGT|ATG|AAG|486|
|Thr|Glu|Arg|Gly|Ser|Ser|Thr|Gly|Lys|Glu|Glu|Gly|Asp|Gly|Met|Lys||
|||135|||||140|||||145||||

|CAG|ATG|GGG|GAG|CTT|GCC|CAG|CAG|TGC|GAA|GGA|GGA|ACA|TAT|GCG|GAC|534|
|Gln|Met|Gly|Glu|Leu|Ala|Gln|Gln|Cys|Glu|Gly|Gly|Thr|Tyr|Ala|Asp||
||150|||||155|||||160|||||

|TTG|CTT|GTC|GAA|GCA|GAG|CAA|GCT|GTT|GTA|CAT|TCC|GTT|CGC|GCA|TTA|582|
|Leu|Leu|Val|Glu|Ala|Glu|Gln|Ala|Val|Val|His|Ser|Val|Arg|Ala|Leu||
||165|||||170|||||175|||||

|ATG|CTG|GCC|GAA|AGA|CAA|AAC|CCA|AAT|ATA|TTG|GGG|GAG|CAT|TTG|AAT|630|
|Met|Leu|Ala|Glu|Arg|Gln|Asn|Pro|Asn|Ile|Leu|Gly|Glu|His|Leu|Asn||
|180||||185|||||190|||||195|||

|AAA|AAA|CGG|GTT|CTT|GTA|CAA|CGA|CCC|CGT|ACT|ATT|CTA|TCC|GTG|GAG|678|
|Lys|Lys|Arg|Val|Leu|Val|Gln|Arg|Pro|Arg|Thr|Ile|Leu|Ser|Val|Glu||
||||200|||||205|||||210|||

|TCA|GAG|AAT|GCA|ACA|ATG|CGT|TCT|TAT|ATG|CTG|GTT|ACA|TTG|ATA|TGT|726|
|Ser|Glu|Asn|Ala|Thr|Met|Arg|Ser|Tyr|Met|Leu|Val|Thr|Leu|Ile|Cys||
|||215|||||220|||||225||||

|TCT|GCA|AAA|TCA|TTA|TTA|CTA|GGA|TCG|TGC|ATG|TCA|TTT|TTC|GCT|GGT|774|
|Ser|Ala|Lys|Ser|Leu|Leu|Leu|Gly|Ser|Cys|Met|Ser|Phe|Phe|Ala|Gly||
|||230|||||235|||||240||||

|ATG|TTA|GTC|GGT|AGA|ACG|GCA|GAC|GTA|AAA|ACA|CCA|TTA|TGG|GAT|ACT|822|
|Met|Leu|Val|Gly|Arg|Thr|Ala|Asp|Val|Lys|Thr|Pro|Leu|Trp|Asp|Thr||
||245|||||250|||||255|||||

|GTA|TGT|TTG|TTA|ATG|GCT|TTC|TGT|GCA|GGC|ATT|GTC|GTT|GGG|GGA|GTG|870|
|Val|Cys|Leu|Leu|Met|Ala|Phe|Cys|Ala|Gly|Ile|Val|Val|Gly|Gly|Val||
|260||||265|||||270|||||275|||

|GAT|TCT|GGG|GAG|GTG|GAA|TCT|GGA|GAA|ACA|AAA|TCT|GAA|TCA|AAT||915|
|Asp|Ser|Gly|Glu|Val|Glu|Ser|Gly|Glu|Thr|Lys|Ser|Glu|Ser|Asn|||
||||280|||||285|||||290|||

TAAATTTAAT ACAGTGTAGC CGTACCCGAC GTTGGAGGCG GAGATTAAGC GAATTCTCAC 975

( 2 ) INFORMATION FOR SEQ ID NO:2:

( i ) SEQUENCE CHARACTERISTICS:
    ( A ) LENGTH: 290 amino acids
    ( B ) TYPE: amino acid
    ( D ) TOPOLOGY: linear ( i i ) MOLECULE TYPE: protein (x i) SEQUENCE DESCRIPTION: SEQ ID NO:2:

```
Met Glu Phe Glu Ala Glu His Glu Gly Leu Thr Ala Ser Trp Val Ala
 1               5                  10                  15
Pro Ala Pro Gln Gly Gly Lys Gly Ala Glu Gly Arg Ala Gly Val Ala
            20                  25                  30
Asp Glu Ala Gly His Gly Lys Thr Glu Ala Glu Cys Ala Glu Asp Gly
            35                  40                  45
Glu Lys Cys Gly Asp Ala Glu Met Ser Ala Leu Asp Arg Val Gln Arg
    50                  55                  60
Asp Arg Trp Arg Phe Ser Ser Pro Pro Pro His Ser Gly Val Thr Gly
65                  70                  75                  80
Lys Gly Ala Ile Pro Ile Lys Gly Asp Gly Lys Ala Ile Glu Cys Gln
                85                  90                  95
Glu Leu Thr Gly Glu Gly Glu Trp Leu Ser Gln Trp Glu Glu Leu Pro
            100                 105                 110
Pro Glu Pro Arg Arg Ser Gly Asn Glu His Leu Asp Glu Ser Arg Tyr
            115                 120                 125
Ala Lys Gln Thr Glu Arg Gly Ser Ser Thr Gly Lys Glu Glu Gly Asp
    130                 135                 140
Gly Met Lys Gln Met Gly Glu Leu Ala Gln Gln Cys Glu Gly Gly Thr
145                 150                 155                 160
Tyr Ala Asp Leu Leu Val Glu Ala Glu Gln Ala Val Val His Ser Val
                165                 170                 175
Arg Ala Leu Met Leu Ala Glu Arg Gln Asn Pro Asn Ile Leu Gly Glu
            180                 185                 190
His Leu Asn Lys Lys Arg Val Leu Val Gln Arg Pro Arg Thr Ile Leu
        195                 200                 205
Ser Val Glu Ser Glu Asn Ala Thr Met Arg Ser Tyr Met Leu Val Thr
    210                 215                 220
Leu Ile Cys Ser Ala Lys Ser Leu Leu Leu Gly Ser Cys Met Ser Phe
225                 230                 235                 240
Phe Ala Gly Met Leu Val Gly Arg Thr Ala Asp Val Lys Thr Pro Leu
                245                 250                 255
Trp Asp Thr Val Cys Leu Leu Met Ala Phe Cys Ala Gly Ile Val Val
            260                 265                 270
Gly Gly Val Asp Ser Gly Glu Val Glu Ser Gly Glu Thr Lys Ser Glu
            275                 280                 285
Ser Asn
290
```